(12) United States Patent
Rothenberger et al.

(10) Patent No.: US 8,186,998 B2
(45) Date of Patent: May 29, 2012

(54) BLANK-HOLDING MEANS AND METHOD OF SURVEYING SAME

(75) Inventors: Bernd Rothenberger, Gernsbach (DE); Reinhard Pieper, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 10/847,669

(22) Filed: May 18, 2004

(65) Prior Publication Data
US 2005/0008989 A1   Jan. 13, 2005

(30) Foreign Application Priority Data
May 19, 2003  (DE) .................... 103 22 762

(51) Int. Cl.
*A61C 1/14* (2006.01)
(52) U.S. Cl. ........................................... 433/49
(58) Field of Classification Search ............. 433/49, 433/50, 51; 264/16, 19; 269/287
See application file for complete search history.

(56) References Cited

U.S. PATENT DOCUMENTS

| | | | |
|---|---|---|---|
| 3,665,493 A | 5/1972 | Glowzewski et al. | |
| 4,615,678 A | 10/1986 | Moermann et al. | |
| 4,988,297 A | 1/1991 | Lazzara et al. | |
| 5,092,022 A | 3/1992 | Duret | |
| 5,273,429 A | 12/1993 | Rekow et al. | |
| 5,342,696 A * | 8/1994 | Eidenbenz et al. | 428/542.8 |
| 5,359,511 A | 10/1994 | Schroeder et al. | |
| 5,378,091 A | 1/1995 | Nakamura | |
| 5,556,278 A | 9/1996 | Meitner | |
| 5,716,215 A | 2/1998 | Blacklock | |
| 5,788,494 A | 8/1998 | Phimmasone | |
| 5,846,079 A | 12/1998 | Knode | |
| 5,989,029 A | 11/1999 | Osorio et al. | |
| 6,126,445 A | 10/2000 | Willoughby | |
| 6,142,782 A | 11/2000 | Lazarof | |
| 6,224,371 B1 | 5/2001 | De Luca | |
| 6,231,342 B1 | 5/2001 | Osorio et al. | |
| 6,354,836 B1 | 3/2002 | Panzera et al. | |
| 6,394,880 B1 | 5/2002 | Basler et al. | |
| 6,398,554 B1 | 6/2002 | Perot et al. | |
| 6,482,284 B1 * | 11/2002 | Reidt et al. | 156/200 |
| 6,485,305 B1 * | 11/2002 | Pfeiffer | 433/202.1 |
| 6,640,150 B1 | 10/2003 | Persson et al. | |
| 6,666,684 B1 | 12/2003 | Names | |

(Continued)

FOREIGN PATENT DOCUMENTS

AU    762679 B2    7/2003

(Continued)

OTHER PUBLICATIONS

Brian K.S. Kucey et al., "The Procera Abutment—The Fifth Generation Abutment for Dental Implants," Journal of Canadian Dental Association, vol. 66, No. 8, pp. 445-449 (Sep. 2000).

(Continued)

*Primary Examiner* — Sunil K Singh
(74) *Attorney, Agent, or Firm* — Fitzpatrick, Cella, Harper & Scinto

(57) ABSTRACT

The invention relates to holding means for a blank for the production of dental fitted shells, including connection geometry for the blank and a shaft for attachment thereof in a chuck of a processing machine. The holding means has, above the shaft, survey geometry, the orientation of the connection geometry relative to the survey geometry being known.

7 Claims, 3 Drawing Sheets

U.S. PATENT DOCUMENTS

| | | |
|---|---|---|
| 6,788,986 B1 | 9/2004 | Traber et al. |
| 6,968,247 B2 | 11/2005 | Rathke et al. |
| 6,970,760 B2 | 11/2005 | Wolf et al. |
| 7,086,863 B2 | 8/2006 | Van der Zel |
| 7,226,338 B2 | 6/2007 | Duncan et al. |
| 2002/0090592 A1 | 7/2002 | Riley et al. |
| 2003/0073394 A1 | 4/2003 | Reidt et al. |
| 2006/0106484 A1 | 5/2006 | Saliger et al. |
| 2006/0141250 A1 | 6/2006 | Basler et al. |
| 2006/0292527 A1 | 12/2006 | Basler et al. |
| 2007/0050072 A1 | 3/2007 | Schwotzer |
| 2009/0273108 A1 | 11/2009 | Koebel et al. |

FOREIGN PATENT DOCUMENTS

| | | |
|---|---|---|
| CA | 2322761 A1 | 9/1999 |
| DE | 19612699 C1 | 7/1997 |
| DE | 19654055 A1 | 6/1998 |
| DE | 197 33 161 C2 | 2/1999 |
| DE | 10330758 A1 | 2/2005 |
| DE | 102004063417 A1 | 7/2006 |
| DE | 102006052027 A1 | 5/2008 |
| EP | 0 160 797 | 11/1985 |
| EP | 0455854 A1 | 11/1991 |
| EP | 0850601 A2 | 7/1998 |
| EP | 0904743 A2 | 3/1999 |
| EP | 1 023 876 | 8/2000 |
| EP | 1062916 A2 | 12/2000 |
| EP | 1252867 A1 | 10/2002 |
| EP | 1067880 A1 | 10/2003 |
| EP | 1658825 A1 | 5/2006 |
| JP | 10277059 | 10/1998 |
| WO | 99/13796 | 3/1999 |
| WO | 9947065 A1 | 9/1999 |
| WO | 0135854 A1 | 5/2001 |
| WO | 03007834 A1 | 1/2003 |
| WO | 03024352 A1 | 3/2003 |
| WO | 2004060197 A1 | 7/2004 |
| WO | 2005002463 A1 | 1/2005 |

OTHER PUBLICATIONS

European Patent Office, "Internationaler Vorlaufiger Bericht Uber Die Patentierbarkeit" issued in International Application No. PCT/EP2008/060043, 6 pages, Oct. 19, 2009 (and English translation thereof).

European Patent Office, "Schriftlicher Bescheid Der Internationalen Recherchenbehorde" in connection with International Application No. PCT/EP2009/053999, 6 pages, Oct. 3, 2010 (and English translation thereof).

At least partial English translation of Office Action issued Feb. 12, 2009, by the German Patent Office in connection with International Application No. PCT/EP2009/053999, 2 pages.

U.S. Patent and Trademark Office, Office Action dated Apr. 20, 2009, in connection with U.S. Appl. No. 10/557,153, 11 pages.

U.S. Patent and Trademark Office, Office Action dated Oct. 14, 2009, in connection with U.S. Appl. No. 10/557,153, 12 pages.

U.S. Patent and Trademark Office, Office Action dated Mar. 11, 2010, in connection with U.S. Appl. No. 10/557,153, 13 pages.

U.S. Patent and Trademark Office, Office Action dated Nov. 23, 2010, in connection with U.S. Appl. No. 10/557,153, 16 pages.

* cited by examiner

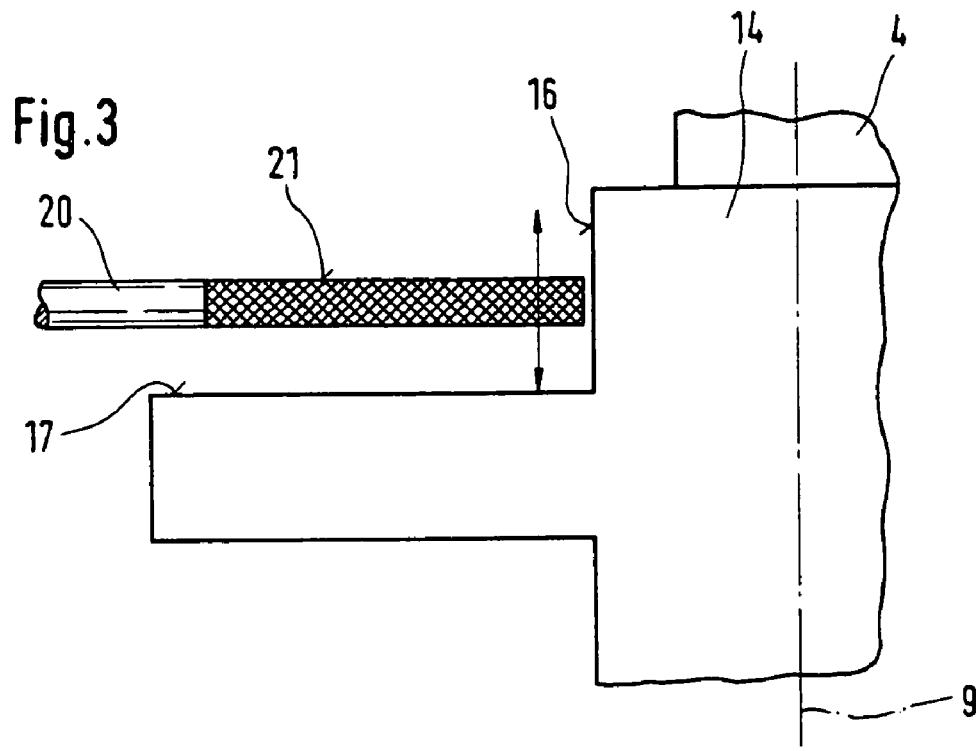
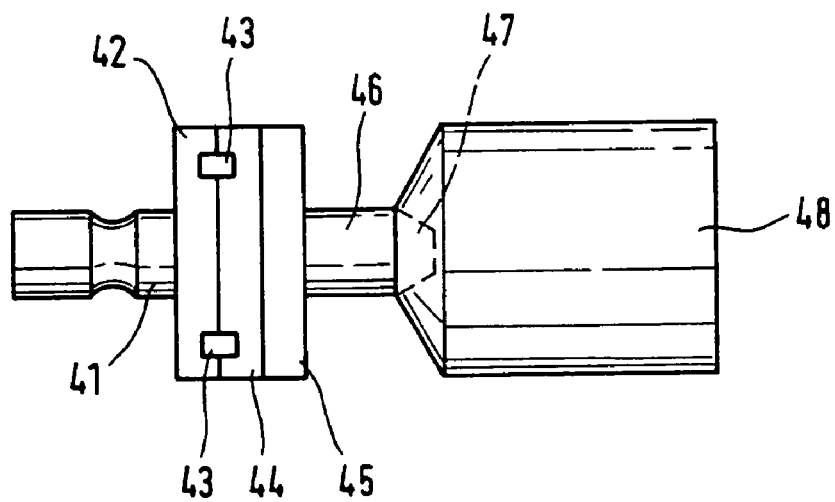

BLANK-HOLDING MEANS AND METHOD OF SURVEYING SAME

RELATED APPLICATIONS

This application claims benefit of priority of German Patent Application No. 103 22 762.8, filed May 19, 2003.

TECHNICAL FIELD

The invention relates to a holding means for a blank for the production of dental fitted shells and having connection geometry for the blank and a shaft to be clamped in a chuck of a processing machine and to a method of determining the position and orientation of (surveying) connection geometry provided on a holding means for a blank releasably attached to said holding means, particularly a blank for the production of dental fitted shells, which holding means is clamped by way of its shaft in a chuck in a processing machine and is at least roughly aligned in space with reference to the chuck axis, and various points of a survey geometry on said holding means are contacted by a processing instrument.

BACKGROUND OF THE INVENTION

When machining a ceramic block having preformed connection geometry, as disclosed, for example, in EP 1 023 876 A2, the position and orientation of said geometry relative to the geometry of the processing machine must be known. However, the connection geometry itself cannot always be directly surveyed, since an optical surveying device is not always present.

For this reason, ceramic blocks having preformed connection geometry have either not been processed mechanically, or the shape to be machined has not required, for reasons of symmetry, any precise knowledge of the position and shape of the preformed geometry.

In the field of fabricating dental fitted shells from blanks in the form of ceramic blocks, EP 0 160 797 A1 discloses a method of causing the processing tool to contact a specially calibrated area of a holding means for the blank and thus of utilizing the processing tool for locating the position of the center axis of the blank with reference to the processing tool. Preferably, the holding means itself should be shaped such that it is automatically accurately positioned in the processing machine by means of reference stops.

A drawback of this is that it is not possible to precisely locate the position of the abrasive tools relative to the blank, as is necessary for machining blanks having a preformed connection geometry.

The object of the invention consists in making it possible to machine ceramic blocks having a preformed connection geometry and to mechanically fabricate any desired symmetrical or asymmetrical shape from such a block.

SUMMARY OF THE INVENTION

According to the invention, the holding means has, above its shaft, a survey geometry, the orientation of the connection geometry relative to said survey geometry being known.

Thus it is possible to effect, by way of the holding means, precise measurement of the dimensions relevant for locating the position of the connection geometry, by which means the position and orientation of the block geometry can be indirectly measured where direct measurement is not possible.

Advantageously, the survey geometry comprises a surface normal to the longitudinal axis of the holding means and a plane lateral surface parallel to said longitudinal axis.

According to a further development, the survey geometry contains information on the type of connection geometry involved. This makes it possible to check whether the correct type is fixed in the processing machine.

Another object of the invention is a blank for the production of a dental fitted shell, which blank has preformed connection geometry and, in addition, survey geometry, the orientation of the connection geometry relative to the survey geometry being known. Here again, the survey geometry can contain information on the type of connection geometry involved.

Advantageously, the blank has a region for attachment to a processing machine and the connection geometry is oriented relative to said attachment region such that the connection geometry is accessible for surveying when the blank is secured in the processing machine. Thus surveying can be readily carried out and it is possible to detect, if necessary, whether the inserted block is suitable for processing.

The present method of determining the position and orientation of (surveying) the connection geometry located on holding means for a blank releasably attached to said holding means, in particular for the production of a dental fitted shell, consists in determining the position and orientation of said connection geometry by surveying survey geometry whose position and orientation relative to said connection geometry is known.

Advantageously, this purpose is achieved by surveying survey geometry provided on the blank.

Another object of the invention consists in a method of determining the position and orientation of implant-specific connection geometry of a blank for the production of a dental fitted shell, in which the blank is secured in a processing machine such that the connection geometry is accessible for surveying, and surveying of said connection geometry is carried out.

Advantageously, the blank is connected, for the purpose of attachment to a processing machine, to holding means, part of said holding means being connected to the processing machine. This has the advantage that the holding means can be of a different material and that one and the same holding means can be used for a plurality of blanks.

Another object of the invention consists in a method of determining the position and orientation of connection geometry located on holding means for a blank releasably attached to said holding means for the production of a dental fitted shell, wherein said holding means is clamped by way of its shaft in a chuck of a processing machine and an at least rough spatial alignment thereof relative to the chuck axis is given, and various points of a survey geometry of said holding means are contacted by a processing instrument.

The amount of longitudinal displacement of the connection geometry with respect to the longitudinal axis of the shaft is measured by at least one contacting operation with respect to a surface of said holding means normal to said longitudinal axis and the extent of rotation of said connection geometry about said longitudinal axis and also the degree of eccentricity of said connection geometry with reference to said longitudinal axis are determined by at least one contacting operation directed toward a plane lateral surface parallel to the longitudinal axis of said holding means, and the position and orientation of said connection geometry of said holding means relative to said blank are deduced from the readings obtained by said measurements.

A final object the invention consists in a method of determining the position and orientation of connection geometry located on holding means for a blank releasably attached to said holding means for the production of a dental fitted shell, wherein said holding means is clamped by way of its shaft in a chuck of a processing machine and an at least rough spatial alignment thereof relative to the chuck axis is given. By means of a measuring device various points of the survey geometry on the holding means are surveyed.

In order to determine the amount of longitudinal displacement of the connection geometry with respect to the longitudinal axis of the shaft, at least one surface of said holding means normal to said longitudinal is surveyed and the extent of rotation of said connection geometry about said longitudinal axis, and the degree of eccentricity of said connection geometry with reference to said longitudinal axis, a plane lateral surface parallel to the longitudinal axis of said holding means is surveyed, and the position and orientation of said connection geometry of said holding means relative to said blank are deduced from the readings obtained by said surveying measurements.

One procedure thus involves carrying out a contacting operation, for example, with a processing tool, whilst another procedure involves contactless surveying.

The basic method, as carried out in practice, may be described as follows:

in a first step, the holding means is inserted with its shaft in the chuck of a processing machine, so that at least rough spatial alignment thereof with reference to the chuck axis is achieved, in the second step, the shaft is clamped in the chuck, and in a third step, various points of the survey geometry of the holding means are surveyed with a processing instrument or in some other way.

Exact determination of the position of the holding means in the chuck is thus made possible by measuring the amount of longitudinal displacement of the connection geometry with respect to the longitudinal axis of the shaft by means of at least one contacting or surveying operation directed toward a surface normal to the longitudinal axis of the holding means, and by determining the extent of rotation of the connection geometry about the longitudinal axis by means of at least one contacting or surveying operation directed toward a plane lateral surface parallel to the longitudinal axis of the holding means, and by deducing, in a fourth step, the position and orientation of the connection geometry of the holding means relative to the blank from the readings obtained by such surveying. This surveying operation can be carried out without contacting any surface, if desired.

The aforementioned device satisfies four requirements. Firstly, the holding means is adapted, by reason of its securing geometry, to be clamped in rough orientation in the chuck of a processing machine. In the present embodiment this requirement is satisfied by a shaft and a disk provided with a notch.

Secondly, the holding means is configured such that it can be positively connected, via the connection geometry, to the preformed geometry of the ceramic block. In the present embodiment this requirement is satisfied in that the preformed geometry of the blank is present in negative form. The holding means positively engages the preformed geometry of the blank via the connection geometry.

The symmetry of the blank including any preformed geometry can be represented by the shape of the holding means. Multidentate symmetry need not be unequivocally resolved. If the block is, say, axially symmetrical and the preformed symmetry is hexa- or octa-dentate, the connection between the holding means and the blank will likewise have a hexa- or octa-dentate symmetry, which need not be further resolved.

Theoretically, any type of connection geometry can be used for the attachment of the holding means to the blank, provided it permits neither translational nor rotational displacements of the blank relatively to the holding means. A multidentate symmetry is possible but should be designed such that accidental mounting of an asymmetrical blank in a direction not conforming to the proper securing direction will be immediately optically apparent to the user.

Thirdly, the holding means is adapted to allow for surveying of the survey geometry. In the present embodiment this requirement is satisfied in that mechanical surveying of the device is made possible by suitable geometry. This surveying takes into account and measures all tolerances permitted by the type of fixture, eg, translational, rotational, and eccentric tolerances.

Fourthly, the holding means is designed such that surveying of the survey geometry makes it possible to clearly deduce the position and orientation of the connection geometry.

Furthermore, the survey geometry can be designed such that the type of connection geometry is coded in the survey geometry as a feature of the implant to be supplied.

WO 99/13796 discloses a method of surveying a surface mounted on a holding means by means of a laser beam and interpreting the length and width or the axial length and the distance from the center axis as an identification of the type of blank used, but this is carried out prior to moving the holding means toward the processing machine.

BRIEF DESCRIPTION OF THE DRAWINGS

The holding means and method of the invention are explained below with reference to the drawings, in which FIG. 3 shows a processing tool for surveying the holding means, FIG. 4 shows split holding means.

EMBODIMENT ACCORDING TO THE INVENTION

Figure 1:
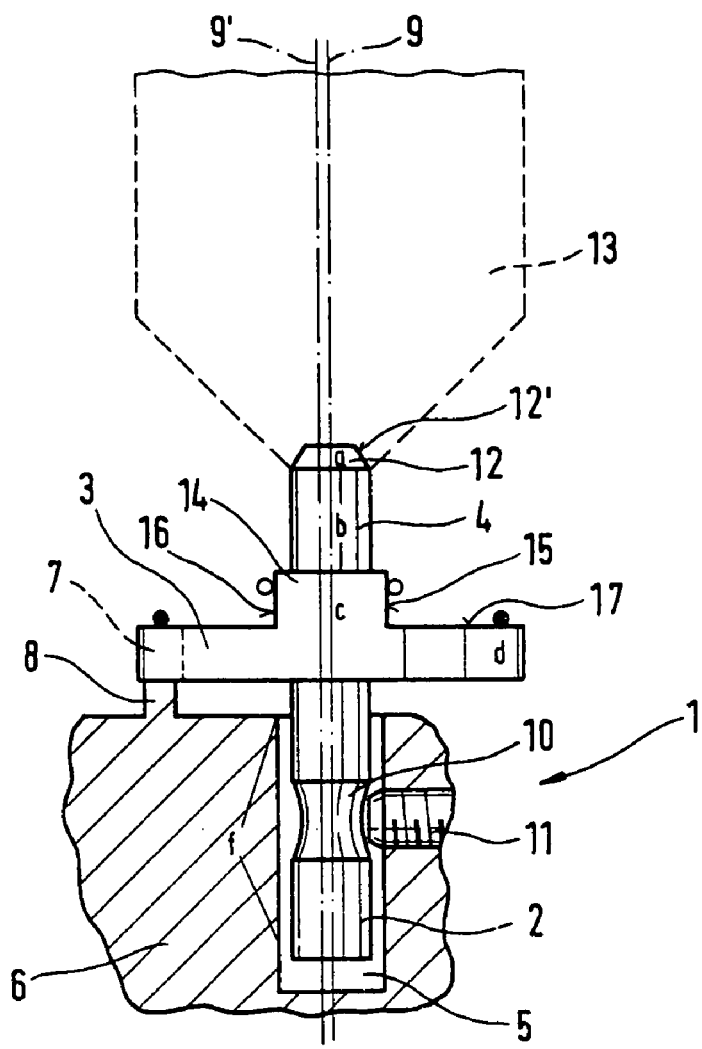
FIG. 1 is a side view of a holding means for a blank.

The holding means 1 shown in FIG. 1 comprises a shaft 2, a disk 3, and an extension 4. The securing geometry of shaft 2 is free to vary in several ways.

By reason of a vaguely defined position of a stop member 5 disposed at the end of shaft 2 in a workholding device, the position of shaft 2 in the accommodating chuck 6 may vary in the longitudinal direction of the shaft.

Since only rough prepositioning is achieved by the engagement of an alignment pin 8 in a locking notch 7 in the disk 3, rotational displacement about the longitudinal axis 9 of the accommodating chuck 6 is possible.

By reason of the fact that shaft 2 is secured in chuck 6 by means of a grub screw 11 acting on a securing region 10 on the periphery of the shaft, asymmetrical fixation of the securing geometry in the chuck 6 can cause eccentricity with reference to the longitudinal axis 9 of chuck 6.

In order to be able to put shaft 2 into chuck 6, the radius of shaft 2 must necessarily be smaller than the internal radius of chuck 6. These radii are usually subject to batch variations. Fixing by means of grub screw 11 from the side thus leads to an undefined degree of eccentricity between the longitudinal axis 9' of shaft 2 and the longitudinal axis 9 of chuck 6. Since shaft 2 is itself a precision turned part and connection geometry 12 is also in precise concentric alignment with shaft 2, the connection geometry will be eccentrically mounted with respect to longitudinal axis 9 of the chuck.

The aforementioned tolerances all contribute to the fact that the position of connection geometry 12 for a blank 13 is not reliably reproducible. If an implant or skeletal framework is to be machined out of blank 13, however, all of said geometrical interrelations will be significant.

Figure 2:
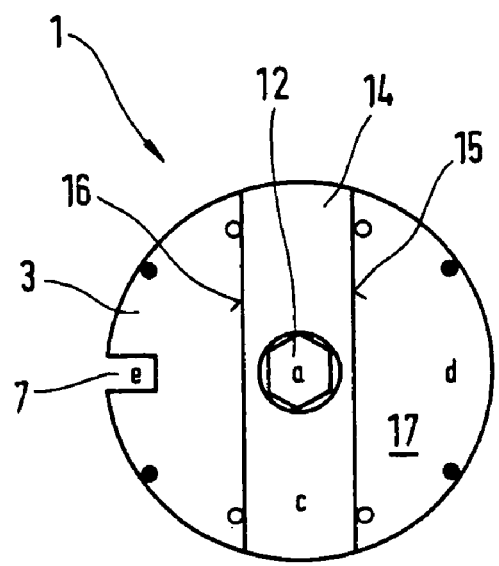
FIG. 2 is a top view of the holding means of FIG. 1.

FIG. 2 shows, besides the features already described, some other features of holding means 1. In its center there is situated connection geometry 12 for the blank (not shown). The dimensions of said connection geometry 12 conform to the prior art. Also visible is disk 3 with locking notch 7 on its perimeter.

A beam 14 having lateral surfaces 15, 16 is shown as being part of the survey geometry. Lateral surfaces 15, 16 are oriented in parallelism. As may be seen from FIG. 1, lateral surfaces 15, 16 also extend parallel to, and at a distance from, longitudinal axis 9' of holding means 1.

The top surface 17 of disk 3 is part of the survey geometry and is disposed normal to the longitudinal axis of holding means 1.

The surveying device used for locating the position of holding means 1 fixed in chuck 6 is a processing tool 20 of a processing machine illustrated in FIG. 3. This tool 20 is moved toward the various reference surfaces 16, 17 of the survey geometry at a slow feed rate and a very slow rotatory speed until mechanical contact between tool 20 and reference surface 16, 17 retards the speed of rotation. This contacting method is known per se from the prior art and makes it possible to deduce the position of the reference surface by computation based on the knowledge of the position of the tool.

The survey geometry in this case consists of top surface 17 of the disk and a lateral surface 16 of beam 14, said lateral surface being parallel to longitudinal axis 9.

The amount of longitudinal displacement along shaft 2 is surveyed by at least one contacting operation on the top surface 17 of disk 3, suitable surveying points being indicated in FIGS. 1, 2 by filled circles. In this case contact is achieved by the lateral surface 21 of processing tool 20. If top surface 17 of disk 3 is a plane surface which is also normal to longitudinal axis 9 of chuck 6, the point at which the top surface is contacted is theoretically insignificant.

Rotation of the holding means about longitudinal axis 9 and the degree of eccentricity of the holding means with reference to this axis can be determined by a number of contacting operations directed toward lateral surfaces 15, 16 of beam 14. The quality of the surveying operation is improved the further away the points of contact are from the beam. Suitable surveying points are indicated in FIG. 1, 2 by circles.

Basically, optical surveying of the survey geometry is alternatively possible.

Due to the fact that holding means 1 is adapted to allow for surveying of the survey geometry to provide precise information on the position and orientation of the connection geometry, the position and orientation of said connection geometry 12 can be calculated from such surveying measurements. The extension 4 between connection geometry 12 and beam 14 allows for free movement of the processing tool while surveying the survey geometry and during subsequent processing.

Once the holding means has been surveyed, the position of blank 13 secured therein is known and an asymmetrical shape can be machined out of the blank. Knowledge of the exact position of the rotation axis of the ceramic block in the coordinate system of the processing machine can be utilized to resolve the shape into profiles radial to this axis. These can then be machined out while rotating the blank about longitudinal axis 9 of the workholding device.

In particular, fabrication of the holding means and connection geometry as a single unit and the resulting precise knowledge of the position and alignment of the connection geometry with reference to the holding means makes it possible to deduce the position and alignment of the blank by surveying the holding means. Theoretically, the holding means may alternatively be composed of a number of parts, provided the appropriate geometrical relationships are maintained.

This procedure guarantees that the finished fitted shell has the desired position and orientation relative to the connection geometry.

A split holding means is illustrated in FIG. 4. Holding means 40 comprises a shaft 41 adapted to be clamped in a processing machine (not shown) and furthermore a disk 42 having centering means 43 for connection to an attachment 44. Only attachment 44 is provided with survey geometry 45, which is exchangeable and attachable to the centering means. In the present embodiment, attachment 44 is open at its center and is mounted on a neck 46 extending away from disk 42. At the end of neck 46 there is provided connection geometry 47 for a blank 48.

Figure 5:
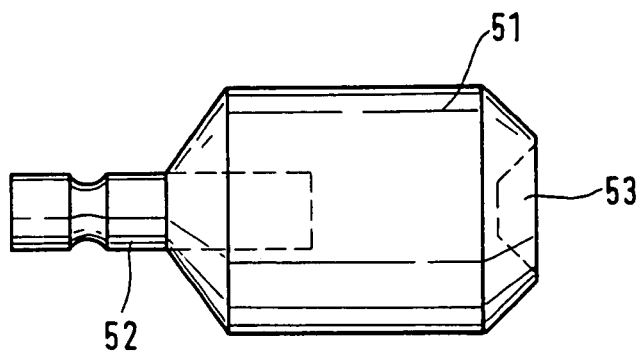
FIG. 5 shows a blank having a shaft for attachment in a workholding device, FIGS. 6a,b show a blank having connection geometry and survey geometry.

FIG. 5 shows a blank 51 that has a shaft 52 for securing in a workholding device. The shaft is of metal and extends into at least a portion of blank 51. Shaft 52 thus represents a metal core that projects from the blank and can be directly clamped. Following processing, shaft 52 is cut off. The connection geometry 53 is disposed at the end of the blank remote from shaft 52.

Figures 6A, 6B:
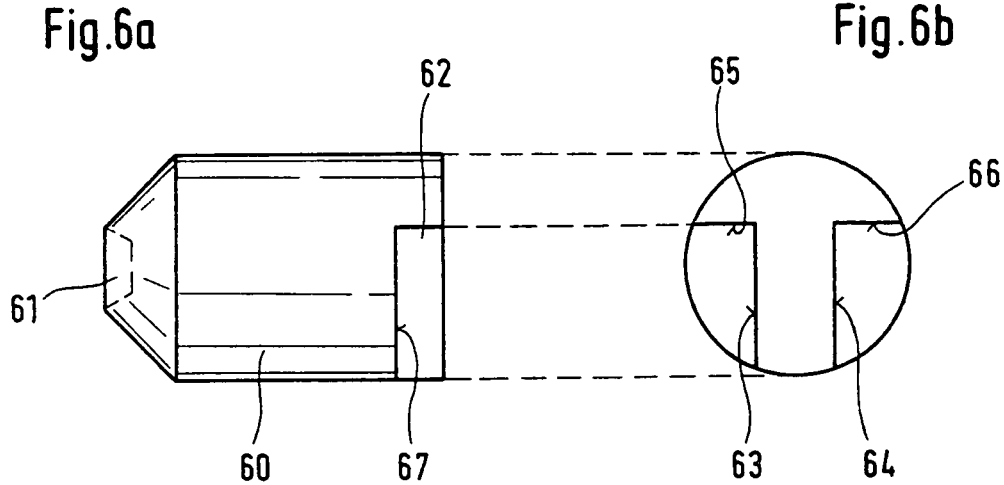

FIG. 6 demonstrates that a blank 60 may be provided not only with connection geometry 61 but also with survey geometry 62. The survey geometry is discernible in the view shown in FIG. 6b and has surfaces 63 to 67 which are comparable to beam 14 and surface 17 of FIG. 1. Surveying these surfaces, or some of them, makes it possible to determine the position of connection geometry 61 with a sufficiently degree of accuracy.

Figure 7:
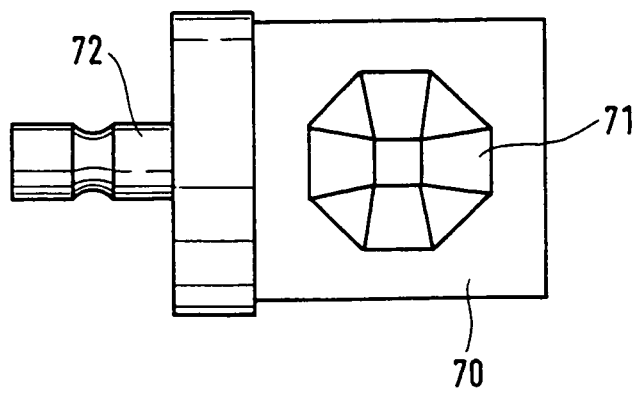
FIG. 7 shows a blank of which the connection geometry is being surveyed.

A blank 70 having connection geometry capable of being surveyed is illustrated in FIG. 7. For this purpose the connection geometry 71 is disposed on the side of blank 70. A shaft 72 extends away from blank 70. When blank 70 is clamped by way of shaft 72 in a workholding device, the connection geometry 71 disposed on the blank itself remains available for surveying. Additional survey geometry is then no longer necessary.

The invention claimed is:

1. A holder for a blank for producing a dental fitted shell, said holder comprising:
    a connection geometry for connecting to the blank;
    a shaft for attaching to a chuck of a processing machine; and
    a survey geometry provided between said shaft and said connection geometry, said survey geometry being separate from said connection geometry, said survey geometry being at least one of connected to another part of said holder and integrally formed as part of said holder, said connection geometry being arranged at a predetermined and fixed orientation relative to said survey geometry before connection of said connection geometry to the blank and maintaining said predetermined and fixed orientation relative to said survey geometry when connected to the blank, and said connection geometry being shaped to engage the blank such that the translational and rotational positioning of the blank relative to the connection geometry once the blank is connected to said connection geometry is fixed and predetermined, and said survey geometry including a surface normal to a longitudinal axis of said holder and at least one planar, lateral surface parallel to said longitudinal axis, said normal and said at least one planar, lateral surfaces being arranged to enable precise surveying of said normal and said at least one planar, lateral surfaces in respective longitudinal and radial directions relative to said longitudinal axis when said blank is attached to said holder, said at least one planar, lateral surface being disposed on a beam that projects upwardly from said surface normal to said longitudinal axis of said holder, said at least one planar, lateral surface being at least one of connected to and integrally formed with said survey geometry for spacing said blank a predetermined distance from said survey geometry.

2. A blank for producing a dental fitted shell, said blank comprising:

a preformed connection geometry;

a region for attaching to a processing machine; and a survey geometry disposed adjacent said region for attaching to the processing machine, said connection geometry being arranged at a predetermined and fixed orientation relative to said survey geometry before attachment of said blank to the processing machine, said predetermined and fixed orientation of said connection geometry relative to said survey geometry being maintained when said blank is connected to the processing machine, and said survey geometry including a generally flat surface normal to and a generally flat surface parallel to a longitudinal axis of said blank, said generally flat surface parallel to said longitudinal axis of said blank extending perpendicularly from said generally flat surface normal to said longitudinal axis of said blank, said generally flat surface normal to said longitudinal axis of said blank enabling precise surveying of said blank in a longitudinal direction relative to said longitudinal axis.

3. A blank as defined in claim 2, wherein said connection geometry is oriented relative to said region for attaching such that said connection geometry is accessible for surveying when said blank is secured in said processing machine.

4. A blank according to claim 2, wherein said connection geometry is shaped to engage the holder such that the translational and rotational positioning of the holder relative to the connection geometry once the holder is connected to said connection geometry is fixed and predetermined.

5. A method of determining a position and an orientation of a connection geometry of a blank for producing a dental fitted shell, said method comprising:

attaching the blank to a processing machine;

determining the position and the orientation of the connection geometry by surveying a survey geometry, wherein the survey geometry is arranged at a non-adjustable, predetermined and known orientation relative to the connection geometry before attachment of the blank to the processing machine, and wherein the predetermined and fixed orientation of the connection geometry relative to the survey geometry is maintained when the blank is connected to the processing machine, and wherein the survey geometry is provided separately from the connection geometry, the survey geometry including a surface normal to a longitudinal axis of the blank and at least one planar, lateral surface parallel to the longitudinal axis, the surface parallel to the longitudinal axis of the blank extending perpendicularly from the surface normal to the longitudinal axis of the blank, the normal and at least one planar, lateral surfaces enabling precise surveying of the blank in respective longitudinal and radial directions relative to the longitudinal axis when the blank is attached to the processing machine.

6. A method of determining a position and an orientation of a connection geometry located on a holder that holds a blank releasably attached to the holder for producing a dental fitted shell, wherein a shaft of the holder is clamped in a chuck of a processing machine, and wherein a rough spatial alignment of the holder relative to a chuck longitudinal axis is given, said method comprising:

surveying one or more portions of a survey geometry of the holder, wherein the survey geometry is arranged at a predetermined position and predetermined and fixed orientation relative to the connection geometry of the holder before connection of the connection geometry to the blank and wherein the predetermined and fixed orientation of the connection geometry relative to the survey geometry is maintained when the connection geometry is connected to the blank, and wherein the connection geometry is shaped to engage the blank such that the translational and rotational positioning of the blank relative to the connection geometry once the blank is connected to the connection geometry is fixed and predetermined; and measuring an amount of longitudinal displacement of the connection geometry with reference to the longitudinal axis of the shaft by at least one contacting operation with respect to a surface normal to the longitudinal axis;

determining an extent of rotation of the connection geometry about the longitudinal axis and a degree of eccentricity of the connection geometry with reference to the longitudinal axis by at least one contacting operation directed toward a planar, lateral surface parallel to the longitudinal axis; and deducing the position and the orientation of the connection geometry of the holder relative to the blank from readings obtained in said surveying and measuring, wherein the survey geometry is provided separately from the connection geometry, the survey geometry including the surface normal to the longitudinal axis and the planar, lateral surface parallel to the longitudinal axis extending perpendicularly from the surface normal to the longitudinal axis, the surface normal to the longitudinal axis and the lateral surface parallel to the longitudinal axis enabling precise surveying of the holder in respective longitudinal and radial directions relative to the longitudinal axis.

7. A method of determining a position and an orientation of a connection geometry located on a holder that holds a blank releasably attached to the holder for producing a dental fitted shell, wherein a shaft of the holder is clamped in a chuck of a processing machine, and wherein a rough spatial alignment of the holder relative to a chuck longitudinal axis is given, said method comprising:

surveying one or more portions of a survey geometry of the holder, wherein the survey geometry is arranged at a predetermined position and predetermined and fixed orientation relative to the connection geometry of the holder before connection of the connection geometry to the blank and wherein the predetermined and fixed orientation of the survey geometry relative to the connection geometry is maintained when the holder is connected to the blank, and wherein the connection geometry is shaped to engage the blank such that the translational and rotational positioning of the blank relative to the connection geometry once the blank is connected to the connection geometry is fixed and predetermined; and surveying a surface normal to the longitudinal axis and measuring an amount of longitudinal displacement of the connection geometry with reference to the longitudinal axis of the shaft;

surveying a planar, lateral surface parallel to the longitudinal axis and determining an extent of rotation of the connection geometry about the longitudinal axis and a degree of eccentricity of the connection geometry with reference to the longitudinal axis; and deducing the position and the orientation of the connection geometry of the holder relative to the blank from readings obtained in said surveying and measuring, wherein the survey geometry is provided separately from the connection geometry, the survey geometry including the surface normal to the longitudinal axis and the planar, lateral surface parallel to the longitudinal axis extending perpendicularly from the surface normal to the longitudinal axis, the surface normal to the longitudinal axis and the planar, lateral surface parallel to the longitudinal axis enabling precise surveying of the holder in respective longitudinal and radial directions relative to the longitudinal axis.

\* \* \* \* \*